United States Patent
Ameen

(10) Patent No.: US 8,635,026 B2
(45) Date of Patent: Jan. 21, 2014

(54) DETERMINATION OF ROCK MECHANICS FROM APPLIED FORCE TO AREA MEASURES WHILE SLABBING CORE SAMPLES

(75) Inventor: Mohammed S Ameen, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 622 days.

(21) Appl. No.: 12/876,634

(22) Filed: Sep. 7, 2010

(65) Prior Publication Data
US 2012/0059590 A1 Mar. 8, 2012

(51) Int. Cl.
*G01V 1/40* (2006.01)
*G01V 3/18* (2006.01)

(52) U.S. Cl.
USPC ............ 702/11; 702/2; 702/6; 702/9; 702/14

(58) Field of Classification Search
USPC .......................................... 702/2, 6, 9, 11, 14
See application file for complete search history.

(56) References Cited

U.S. PATENT DOCUMENTS

| | | | |
|---|---|---|---|
| 4,562,726 A | 1/1986 | Barnaby | |
| 4,628,894 A | 12/1986 | Stewart | |
| 5,216,917 A * | 6/1993 | Detournay | ............... 73/152.59 |
| 5,323,648 A | 6/1994 | Peltier | |
| 5,670,711 A | 9/1997 | Detournay | |
| 7,126,340 B1 | 10/2006 | Ameen | |

OTHER PUBLICATIONS

PCT International Search Report and the Written Opinion for co-pending application No. PCT/US2011/048195, dated Dec. 9, 2011.

* cited by examiner

*Primary Examiner* — Sujoy Kundu
(74) *Attorney, Agent, or Firm* — Bracewell & Giuliani, LLP

(57) ABSTRACT

Mechanical properties of formation rock from a subsurface reservoir are measured with a computerized system while a core sample from the formation is being cut, during a process known as slabbing, for other analytical purposes. Forces exerted during cutting of the slab from the original core sample are sensed and stored in the computer system. The recorded force data, cutting time and dimensions of the core sample and the cut slab are processed in the computer system. Measures of characteristics and mechanical properties of the rock, such as rock strength and angle of internal friction, are obtained with the computer system. Separate and specialized testing procedures performed on test core plugs using samples specially extracted from the original core sample are not required.

13 Claims, 3 Drawing Sheets

DETERMINATION OF ROCK MECHANICS FROM APPLIED FORCE TO AREA MEASURES WHILE SLABBING CORE SAMPLES

BACKGROUND OF THE INVENTION

1. Field of the Invention

The present invention relates to rock material characterization, and in particular to characterization of mechanical properties of formation rock from hydrocarbon reservoirs for geological and engineering purposes such as design and planning of well completion, well testing and formation stimulation.

2. Description of the Related Art

Characterization of the mechanical properties of formation rocks in subsurface hydrocarbon reservoirs has become an important feature for exploration and development of oil and gas. The data obtained from characterization has been used in a variety of ways. Characterization data has been used in well planning and completion and for numerous other purposes. Examples include assessing wellbore stability, hydraulic fracture design, mud weight design, geosteering, reservoir characterization, static and dynamic modeling, and reservoir simulation.

The study of geological strata involved on-site collection of geological samples from rock formations of the strata in the well bore while drilling. Characterization data about the mechanical properties of subsurface rock have been obtained by subjecting rock samples (obtained from geological strata at depths of interest in well bores through formations of interest in the reservoir) to special tests in the laboratory.

The collected geological sample material has been in the form of an elongated cylindrical body of rock known as a core sample. The samples once retrieved to the surface through the well were then transported to laboratories for analysis. The laboratories were by definition at some distance from the well and the samples had to be transferred to the lab for testing.

So far as is known, the rock mechanical properties, including strength of the rock sample have been determined from the core sample by testing what were known as core plugs (small cylindrical plugs) taken from the larger original core sample. The smaller plugs from the reservoir core sample are illustrated for example in U.S. Pat. No. 7,126,340, of which applicant is a named inventor. The core plugs taken would then be tested in various types of specialized rock testing equipment according to data requirements and mechanical properties of interest.

After the plugs were extracted, the larger original core sample was then cut or split along its longitudinal axis to expose the interior stratigraphic profile of the core material in a process which is commonly referred to as "slabbing". The longitudinal section split off from the core sample comprising the core material was often referred to as a "slab". After slabbing, a rock hardness test could then be conducted using what was known as a scratch test to measure another feature of the formation rock, its hardness. A measure of the hardness of formation rock has served as an indication of the resistance of the formation rock to fracture.

The existing methods to assess rock mechanical properties were thus conducted separately before or after the slabbing procedure. This has been time consuming and costly in terms of time and equipment. Further, existing rock characterization testing frequently did not meet short term or urgent operational needs for data necessary for well completion, well testing and stimulation.

SUMMARY OF THE INVENTION

Briefly, the present provides a new and improved computer implemented method of characterizing a mechanical property of formation rock from a subsurface reservoir from a core sample of the rock while the core sample is being cut by a slabbing machine. Data concerning forces applied to the core sample as the sample is being cut are obtained, and a ratio measure of the applied forces to an area measure of the cut sample is formed. An indication of the strength of the formation rock in the core sample is obtained from the formed ratio measure.

Data concerning forces applied in directions normal and tangential to a transverse core sample surface parallel to a longitudinal axis of the core sample are also obtained as the sample is being cut. A ratio measure of the tangential forces to the normal forces applied to the transverse core sample surface is then formed. An indication of the angle of internal friction of the formation rock in the core sample is then obtained from the formed ratio measure of the tangential forces to the normal forces.

The present invention also provides a new and improved data processing system for characterizing a mechanical property of formation rock from a subsurface reservoir from a core sample of the rock while the core sample is being cut by a slabbing machine. The data processing system includes a processor which obtains data concerning forces applied to the core sample as the sample is being cut, forms a ratio measure of the applied forces to an area measure of the cut sample, and obtains from the formed ratio measure an indication of the strength of the formation rock in the core sample. The data processing system also includes a memory storing a record of the obtained indication of the strength of the formation rock in the core sample, and an output device providing an output record of the obtained indication of the strength of the formation rock in the core sample.

The processor of the data processing system according to the present also obtains data concerning forces applied in directions normal and tangential to a transverse core sample surface parallel to a longitudinal axis of the core sample as the sample is being cut, then forms a ratio measure of the tangential forces to the normal forces applied to the transverse core sample surface, and obtains from the formed ratio measure an indication of the angle of internal friction of the formation rock in the core sample. The data processing system also includes a memory storing a record of the obtained indication of the angle of internal friction of the formation rock in the core sample, and an output device providing an output record of the obtained indication of the angle of internal friction of the formation rock in the core sample.

The present invention further provides a data storage device which has stored in a non-transitory computer readable medium therein computer operable instructions causing a data processor to characterize a mechanical property of formation rock from a subsurface reservoir from a core sample of the rock while the core sample is being cut by a slabbing machine. The stored instructions in the data storage device cause the processor to obtain data concerning forces applied to the core sample as the sample is being cut, form a ratio measure of the applied forces to an area measure of the cut sample, and obtain from the formed ratio measure an indication of the strength of the formation rock in the core sample.

The present invention further provides a data storage device which has stored in a non-transitory computer readable medium therein computer operable instructions to cause the processor to obtain data concerning forces applied in directions normal and tangential to a transverse core sample surface parallel to a longitudinal axis of the core sample as the sample is being cut, form a ratio measure of the tangential forces to the normal forces applied to the transverse core sample surface, and obtain from the formed ratio measure of the tangential forces to the normal forces an indication of the angle of internal friction of the formation rock in the core sample.

DETAILED DESCRIPTION OF THE PREFERRED EMBODIMENTS

Figure 1:
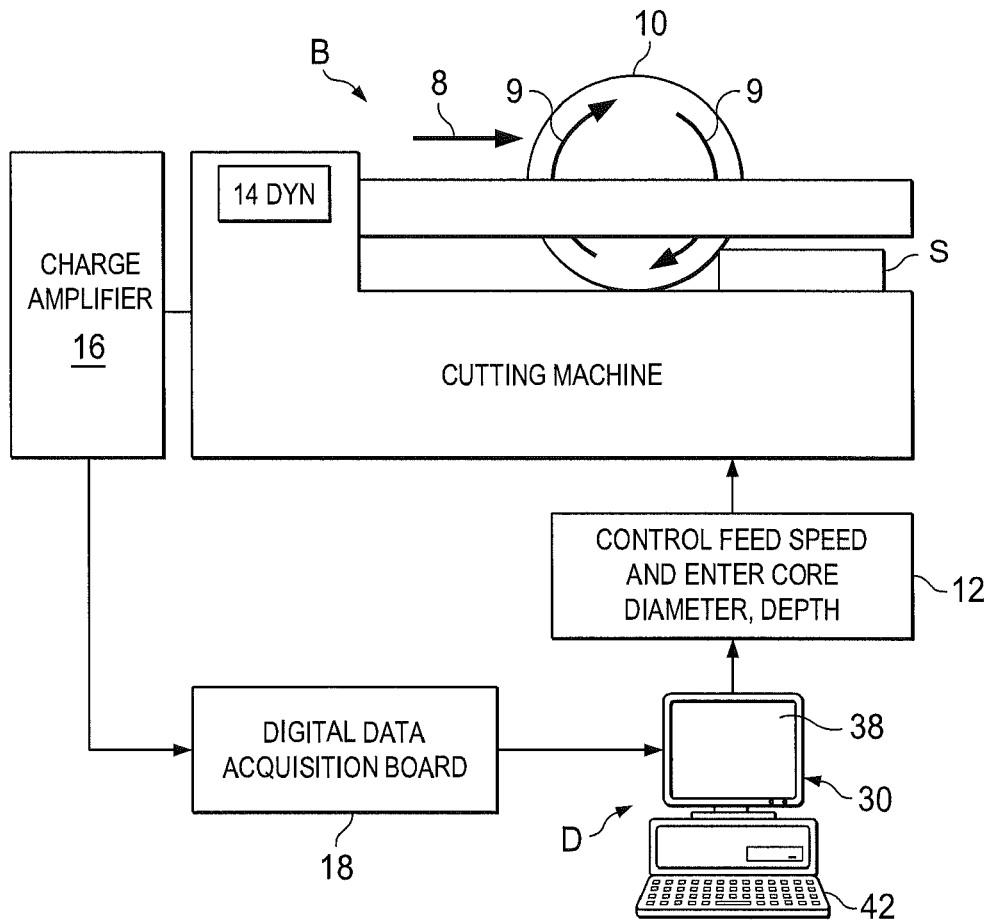
FIG. 1 is a schematic diagram of a computerized system for characterizing mechanical properties of rock according to the present invention.
Figure 2:
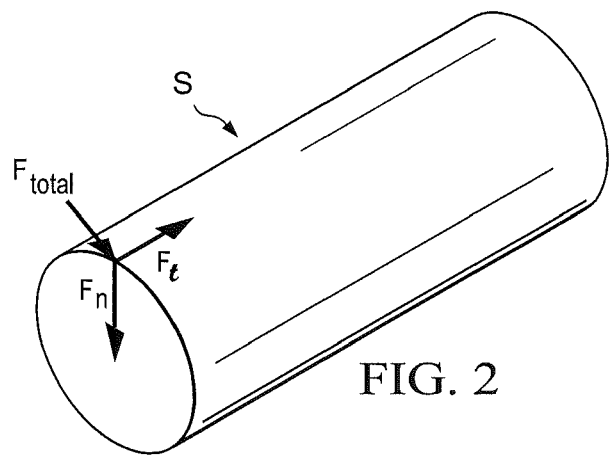
FIG. 2 is an isometric view of a core sample to be characterized in the computer system of FIG. 1.

In the drawings, the letter B designates generally a core slabbing machine in which a core sample S is cut or split along its longitudinal axis to expose the interior stratigraphic profile of the core material. The core sample S is a cylindrical plug or body of formation rock obtained from a subterranean formation of interest and is, for example, usually ≤1 meter or so in length and ≤10 centimeters in diameter. The core sample or plug S is fixedly held in place with machine B while a motor driven saw blade 10 is moved along a longitudinal axis of the core sample S as indicated by an arrow 8. The saw blade 10 is provided with cutting surface of a material with adequate hardness, cutting strength and durability, such as a polycrystalline diamond material. The saw blade 10 is preferably a rotating cutting blade as shown by arrows 9 in FIG. 1, but a motor driven band saw may be used if desired. An example of a slabbing machine is disclosed in U.S. Pat. No. 4,628,894.

The saw blade 10 is mounted and driven by its associated motor for rotational cutting movement as it is advanced with respect to the core sample S for cutting purposes. The cutting procedure performed in the machine B is commonly referred to as "slabbing", and the longitudinal section split off from the core sample is referred to as a "slab".

The cutting machine B is preferably a machine-controlled one which controlled in its speed of movement based on controls provided as indicated schematically at 12, along with other input information, such as dimensions of the sample 5, including its diameter and depth. The cutting machine is controlled to move at a constant rate of speed as it moves along the longitudinal axis of the sample S during cutting.

The core sample S is placed and secured such as by brackets of the conventional type in the machine B and the machine B serves as a rigid tool framework holding the sample in position as the cutting blade 10 advances through the sample during cutting. A conventional force-sensing dynamometer 14 is fixedly mounted with the frame of the machine B to sense forces imparted to the sample by the cutting blade 10 during cutting. The dynamometer is one capable of sensing forces along three mutually perpendicular axes, such as a Kistler 9251A three-dimensional piezoelectric force transducer or dynamometer from Kistler Instrument Corp.

The dynamometer 14 is located at a suitable position on the frame of the machine B and provides as outputs electrical signals corresponding to the magnitude of forces exerted between the saw blade 10 and the core sample S in three vector force measurements. Force measurements are thus obtained for processing according to the present invention as follows: the total force $F_{total}$ exerted to cut the sample core at a constant rate of movement; measurement of the force $F_n$ normal or perpendicular to the direction of such constant movement of the blade 10 to the longitudinal axis of the sample during cutting; and $F_t$ the force parallel to the direction of constant speed cutting movement of the blade 10 to longitudinal axis of the sample S. The transformation of the measured vector forces along the three-dimensional axes into the required force measurements $F_{total}$, $F_n$ and $F_t$ for processing may be performed in the dynamometer/transducer 14 or during subsequent processing.

The electrical signals formed by the dynamometer 14 indicative of forces sensed are transferred to an amplifier bank or circuit 16 composed of separate charge amplifiers for each of the sensed forces. The amplifiers in circuit 16 amplify the force signals and convert them to voltage levels indicative of the sensed forces. The voltage level signals from the charge amplifiers 16 are provided to a data acquisition board 18 where computer compatible digital signals are formed corresponding in digital computer compatible form to the magnitude of forces sensed by the dynamometer 14. The digital signals so formed are transferred to a data processing system D (FIGS. 1 & 3) according to the present invention.

As will be set forth, the data processing system D characterizes a mechanical property or properties of formation rock from a subsurface reservoir from the core sample S of the rock while the core sample is being cut by the slab cutting or slabbing machine B. The mechanical properties obtained according to the present invention include hardness or rock strength and angle of internal friction. Hardness of the core sample (strength) determined according to the present invention is an indication of the resistance of the formation rock to fracture. The angle of internal friction φ or friction angle of the core sample S is a measure of the ability of the formation rock to withstand a shear stress.

Figure 3:
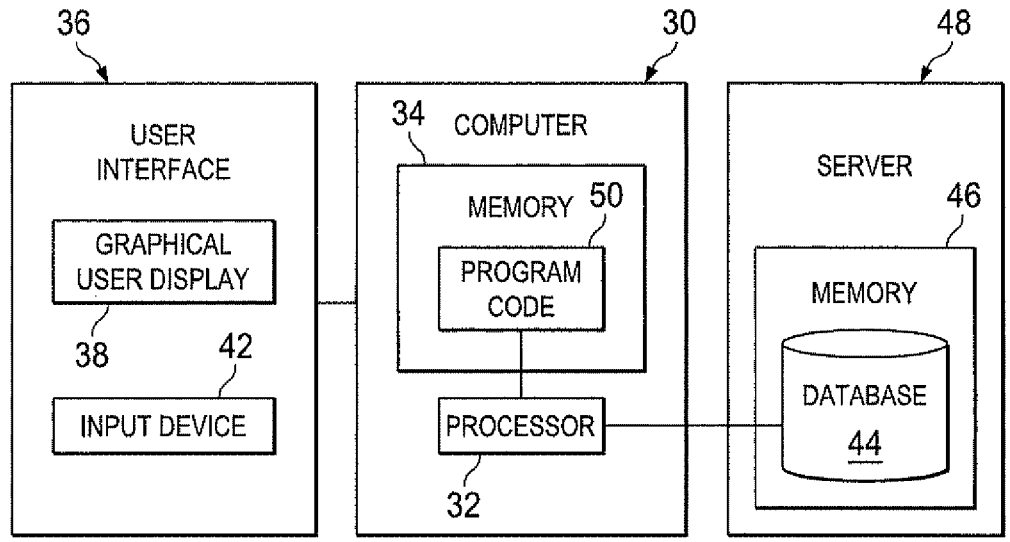
FIG. 3 is a functional block diagram of a computer and associated peripherals of the computer system of FIG. 1 for characterization of mechanical properties of formation rock from a hydrocarbon reservoir according to the present invention.

As illustrated in FIG. 3, the data processing system D includes a computer 30 having a processor 32 and memory 34 coupled to the processor 32 to store operating instructions, control information and database records therein. It should be noted that other digital processors, may be used, such as personal computers in the form of a laptop computer, notebook computer or other suitable programmed or programmable digital data processing apparatus. The processor 32 is however, typically in the form of a personal computer having a user interface 36 and an output display 38 for displaying output data or records of processing of force measurements performed according to the present invention. The output display 38 includes components such as a printer and an output display screen capable of providing printed output information or visible displays in the form of graphs, data sheets, graphical images, data plots and the like as output records or images.

The user interface 36 of computer 30 also includes a suitable user input device or input/output control unit 42 to provide a user access to control or access information and database records and operate the computer 30. Data processing system D further includes a database 44 stored in memory, which may be internal memory 34, or an external, networked, or non-networked memory as indicated at 46 in an associated database server 48. The database 44 can contain various data including: core sample dimensions, such as depth and diameter; movement speed of the saw blade 10; blade movement distance; cutting time measurements; forces as well as conventional data and records used in characterizing mechanical properties of formation rock.

The data processing system D includes program code 50 stored in memory 34 of the computer 30. The program code 50, according to the present invention system 30, is in the form of non-transitory computer operable instructions causing the data processor 32 to characterize mechanical properties of the formation rock of the core sample S while the sample is being cut by a slabbing machine B, as will be set forth.

It should be noted that rock characterization program code 50 may be in the form of microcode, programs, routines, or symbolic computer operable languages that provide a specific set of ordered operations that control the functioning of the data processing system D and direct its operation. The instructions of program code 50 may be may be stored in memory 34 of the computer 30, or on computer diskette, magnetic tape, conventional hard disk drive, electronic read-only memory, optical storage device, or other appropriate data storage device having a non-transitory computer usable medum stored thereon. Program code 50 may also be contained on a data storage device such as server 48 as a non-transitory computer readable medium, as shown.

The computer 30 may also in some cases, if desired, be a mainframe computer of any conventional type of suitable processing capacity such as those available from International Business Machines (IBM) of Armonk, N.Y. or other source. As noted above other digital processors, however, may be used, as well.

Figure 5:
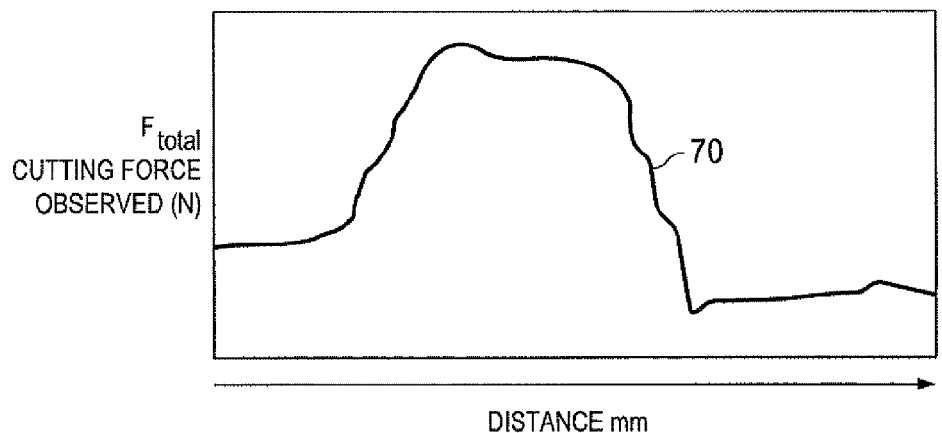
FIG. 5 is a representation of a plot of measured cutting forces of the type obtained according to the present invention.
Figure 6:
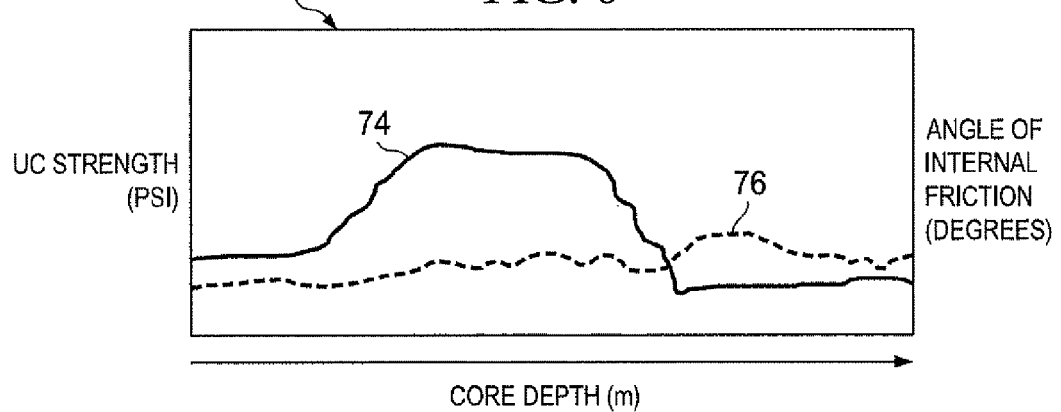
FIG. 6 is a representation of a plots of the type obtained according to the present invention illustrating unconfined compressive (or UC) strength and angle of internal friction of rock as a function of depth of travel through during slabbing

In any case, the processor 32 of the computer 30 accesses the cutting data measurements from the slab cutting machine B to perform the logic of the present invention, which may be executed by the processor 32 as a series of computer-executable instructions. The instructions may also be contained on other forms of data storage device, as described above, with a computer readable medium, such as a computer diskette having a computer usable medium stored thereon containing computer operable instructions. The instructions are computer operable instructions causing the data processor computer 30 to characterize a mechanical property of the core sample S of the rock while the core sample is being cut by the slabbing machine B. The stored instructions are thus a computer program product causing the processor to perform a sequence of steps for this purpose:

The processor 32 of the computer 30 thus receives the data of interest from the slab cutting machine B during slabbing to perform the processing logic of the present invention, which is executed as a series of computer-executable instructions. The results of such processing are then available on output display 38. FIGS. 5 and 6 are examples displays of such result.

A flow chart F (FIG. 4) illustrates the structure of the logic of the present invention as embodied in computer program software. Those skilled in the art will appreciate that the flow charts illustrate the structures of computer program code elements including logic circuits on an integrated circuit that function according to this invention. Manifestly, the invention is practiced in its essential embodiment by a machine component that renders the program code elements in a form that instructs a digital processing apparatus (that is, a computer) to perform a sequence of data transformation or processing steps corresponding to those shown.

It is important to note that, while the present invention has been, and will continue to be, described in the context of a fully functional computer system, those skilled in the art will appreciate that the present invention is capable of being distributed as a program product in a variety of forms, and that the present invention applies equally regardless of the particular type of non-transitory signal-bearing media utilized to actually carry out the distribution. Examples of non-transitory signal-bearing media include: recordable-type media, such as diskettes, hard disk drives, CD ROMs, floppy disks, and tangible media capable of storing the computer operable instructions.

Figure 4:
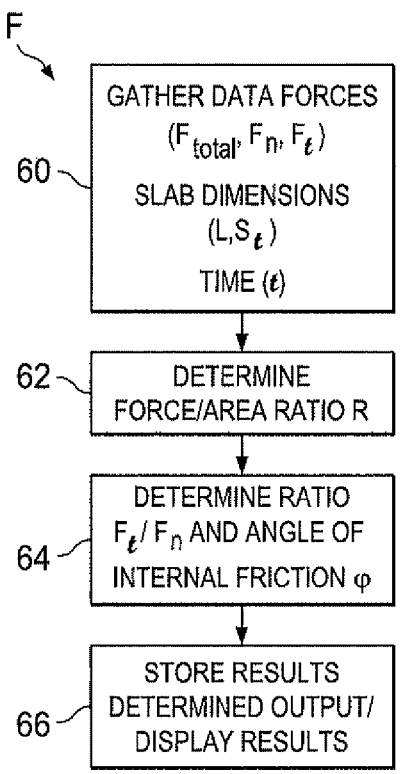
FIG. 4 is a functional block diagram of processing steps for characterization of mechanical properties of formation rock from a hydrocarbon reservoir according to the present invention.

FIG. 4 illustrates schematically a preferred sequence of steps of a process for analyzing a subsurface reservoir of interest to characterize strength (hardness) in formation rock in the reservoir. As shown at step 60, the cutting data and other data and records for characterization of the mechanical properties of the core sample S are assembled for processing. Based on the assembled data, step 62 causes a force to area ratio R as a function of cutting time, or in effect the longitudinal distance of movement of the blade 10 through the sample S to be determined. The ratio R is determined in real time based on the measured force $F_{total}$ to the cross-sectional area of the sample S. The cross sectional are of the slabbed rock (L×T) is correlated with the force $F_{total}$ used in cutting the core sample S. The slope of a plot of the correlation of the ration R is specific to the type of rock and is thus correlated to rock strength. In this way the strength as a mechanical property of the core sample s is characterized in real time as the sample is being slabbed in the machine B. The force to area ratio R values so determined are stored in database 44 and are displayed by display 38.

As indicated at step 64, a ratio $F_t/F_n$ of parallel force $F_t$ to the normal force $F_n$ is determined in real time by the processor 30, as well as a measure of the angle of internal friction $\phi$, again as a function of cutting time or longitudinal distance of movement of the blade 10 through the sample S. During step 66, the results determined in real time during steps 62 and 64 are stored in the database 44 of formation rock characterization records. The results of completed processing, as well as other data and records, are available in real time during slabbing of core sample S, and are also subsequently available for review and analysis as also indicated in step 66. The angle of internal friction $\phi$ as a mechanical property of the core sample S thus also characterized in real time as the sample is being slabbed in the machine B.

The processing results obtained as disclosed above are thus accomplished in real time during slabbing and the data results are readily and quickly available while the core sample is being cut in the slabbing machine B to characterize mechanical properties of formation rock.

FIG. 5 is an example hypothetical display 70 of cutting force $F_{total}$ as a function of distance of along the longitudinal axis of a core sample S recorded continuously during slabbing and obtained according to the present invention. The information content of the display 70 varies according to the nature of the mechanical properties and their characterization of the formation rock under investigation.

FIG. 6 is an example display 72 of mechanical properties: unconfined compressive (or UC) strength as indicated at 74, and the angle of internal friction $\phi$ as indicated at 76, as a function of distance of along the longitudinal axis of the core sample obtained according to the present invention. Again, the information content of the two mechanical properties in display 72 varies according to the nature of character of the formation rock under investigation.

The present invention thus measures mechanical properties of rock samples expediently and promptly. The present invention permits data to be obtained during the conventional process of slabbing the core sample. Thus mechanical properties of the core can be available concurrently while the sample is slabbed for other types of analysis and study.

The present thus saves time and money by simultaneously assessing mechanical properties of the formation rock while performing core slabbing. This enables support of operational needs at short turnaround times and low costs. It optimizes core usage and conserves the core sample for future needs.

The invention has been sufficiently described so that a person with average knowledge in the matter may reproduce and obtain the results mentioned in the invention herein Nonetheless, any skilled person in the field of technique, subject of the invention herein, may carry out modifications not described in the request herein, to apply these modifications to a determined structure, or in the manufacturing process of the same, requires the claimed matter in the following claims; such structures shall be covered within the scope of the invention.

It should be noted and understood that there can be improvements and modifications made of the present invention described in detail above without departing from the spirit or scope of the invention as set forth in the accompanying claims.

What is claimed is:

1. A computer implemented method of characterizing a mechanical property of formation rock from a subsurface reservoir from a core sample of the rock while the core sample is being cut by a slabbing machine, comprising the steps of:
    obtaining data concerning forces applied by the slabbing machine to the core sample as the sample is being cut;
    forming in the computer a ratio measure of the applied forces to an area measure as a function of time during cutting of the sample;
    obtaining in the computer an indication of the strength of the formation rock from the formed ratio measure of the applied forces to area measure in the core sample.

2. The computer implemented method of claim 1, wherein the step of obtaining data comprises:
    obtaining data concerning force vectors applied by the slabbing machine to the core sample as the sample is being cut.

3. The computer implemented method of claim 1, wherein the step of forming a ratio measure further comprises:
    forming a ratio measure of the applied forces to an area measure along the length of the cut sample.

4. The computer implemented method of claim 1, wherein the step of obtaining an indication of the strength of the rock in the core sample comprises:
    obtaining in the computer an indication from the formed ratio measure of the strength of the formation rock along the length of the core sample.

5. The computer implemented method of claim 1, wherein the step of obtaining an indication of the strength of the rock in the core sample comprises:
    obtaining in the computer an indication from the formed ratio measure of the strength of the formation rock as a function of time during cutting of the core sample.

6. The computer implemented method of claim 1, further including the step of:
    storing in memory accessible to the computer a record of the obtained indication of the strength of the formation rock in the core sample.

7. The computer implemented method of claim 1, further including the step of:
    providing an output record of the obtained indication of the strength of the formation rock in the core sample.

8. The computer implemented method of claim 1, further including the steps of:
    obtaining data concerning forces applied by the slabbing machine in directions normal and tangential to a transverse core sample surface parallel to a longitudinal axis of the core sample as the sample is being cut;
    forming in the computer a ratio measure of the tangential forces to the normal forces applied to the transverse core sample surface;
    obtaining in the computer an indication of the angle of internal friction of the formation rock in the core sample from the formed ratio measure of the tangential forces to the normal forces.

9. A data storage device having stored in a non-transitory computer readable medium therein computer operable instructions causing a data processor to characterize a mechanical property of formation rock from a subsurface reservoir from a core sample of the rock while the core sample is being cut by a slabbing machine, the stored instructions in the data storage device causing the processor to perform the following steps:
    obtaining data concerning forces applied to the core sample as the sample is being cut;
    forming a ratio measure of the applied forces to an area measure as a function of time during cutting of the sample;
    obtaining from the formed ratio measure of the applied forces to area measure an indication of the strength of the formation rock in the core sample.

10. A data processing system for characterizing a mechanical property of formation rock from a subsurface reservoir from a core sample of the rock while the core sample is being cut by a slabbing machine, the data processing system comprising:
    a processor performing the steps of:
        obtaining data concerning forces applied to the core sample as the sample is being cut;
        forming a ratio measure of the applied forces to an area measure as a function of time during cutting of the sample;
        obtaining from the formed ratio measure of the applied forces to area measure an indication of the strength of the formation rock in the core sample;
    a memory storing a record of the obtained indication of the strength of the formation rock in the core sample; and
    an output device providing an output record of the obtained indication of the strength of the formation rock in the core sample.

11. A computer implemented method of characterizing a mechanical property of formation rock from a subsurface reservoir from a core sample of the rock while the core sample is being cut by a slabbing machine, comprising the steps of:
    obtaining data concerning forces applied by the slabbing machine to the core sample as the sample is being cut;
    forming in the computer a ratio measure of the applied forces to an area measure of the cut sample;
    obtaining in the computer an indication of the strength of the formation rock from the formed ratio measure of the applied forces to area measure as a function of time during cutting of the core sample.

12. A data storage device having stored in a non-transitory computer readable medium therein computer operable instructions causing a data processor to characterize a mechanical property of formation rock from a subsurface reservoir from a core sample of the rock while the core sample is being cut by a slabbing machine, the stored instructions in the data storage device causing the processor to perform the following steps:
- obtaining data concerning forces applied to the core sample as the sample is being cut;
- forming a ratio measure of the applied forces to an area measure of the cut sample;
- obtaining from the formed ratio measure of the applied forces to area measure an indication of the strength of the formation rock as a function of time during cutting of the core sample.

13. A data processing system for characterizing a mechanical property of formation rock from a subsurface reservoir from a core sample of the rock while the core sample is being cut by a slabbing machine, the data processing system comprising:
- a processor performing the steps of:
  - obtaining data concerning forces applied to the core sample as the sample is being cut;
  - forming a ratio measure of the applied forces to an area measure of the cut sample;
  - obtaining from the formed ratio measure of the applied forces to area measure an indication of the strength of the formation rock as a function of time during cutting of the core sample;
- a memory storing a record of the obtained indication of the strength of the formation rock in the core sample; and
- an output device providing an output record of the obtained indication of the strength of the formation rock in the core sample.

* * * * *